(12) United States Patent
Knowles

(10) Patent No.: US 7,053,529 B2
(45) Date of Patent: May 30, 2006

(54) TORSIONAL ACOUSTIC WAVE SENSOR

(75) Inventor: Terence J. Knowles, Barrington, IL (US)

(73) Assignee: TexZec, Inc., Round Rock, TX (US)

( * ) Notice: Subject to any disclaimer, the term of this patent is extended or adjusted under 35 U.S.C. 154(b) by 30 days.

(21) Appl. No.: 10/611,583

(22) Filed: Jul. 1, 2003

(65) Prior Publication Data
US 2005/0001515 A1    Jan. 6, 2005

(51) Int. Cl.
H01L 41/08    (2006.01)
(52) U.S. Cl. .................. 310/333; 310/328; 310/26
(58) Field of Classification Search ............ 310/328, 310/333; 345/177; 178/18.04; 341/22, 341/34
See application file for complete search history.

(56) References Cited

U.S. PATENT DOCUMENTS

| 4,645,870 | A | 2/1987 | Adler |
| 4,700,176 | A | 10/1987 | Adler |
| 5,149,986 | A | 9/1992 | Jalbert |
| 5,177,327 | A | 1/1993 | Knowles |
| 5,451,723 | A | 9/1995 | Huang et al. |
| 5,573,077 | A | 11/1996 | Knowles |
| 5,673,041 | A | 9/1997 | Chatigny et al. |
| 5,813,280 | A | 9/1998 | Johnson et al. |
| 5,856,820 | A | 1/1999 | Weigers et al. |
| 5,986,224 | A | 11/1999 | Kent |
| 6,078,315 | A | 6/2000 | Huang |
| 6,085,576 | A | 7/2000 | Sunshine et al. |
| 6,087,599 | A | 7/2000 | Knowles |
| 6,091,406 | A | 7/2000 | Kambara et al. |
| 6,369,806 | B1 | 4/2002 | Endo et al. |
| 6,473,075 | B1 | 10/2002 | Gomes et al. |
| 2003/0114760 | A1* | 6/2003 | Robinson .................. 600/459 |
| 2004/0227740 | A1* | 11/2004 | Knowles et al. ............ 345/177 |
| 2004/0246239 | A1* | 12/2004 | Knowles et al. ............ 345/177 |
| 2005/0016278 | A1* | 1/2005 | Knowles et al. ............. 73/592 |

OTHER PUBLICATIONS

"Trapped Torsional Modes In Solid Cylinders," W. Johnson, B.A. Auld and E. Segal, J. Acoustic. Soc. Am. (1), Jul. 1996.

* cited by examiner

Primary Examiner—Thomas M. Dougherty
(74) Attorney, Agent, or Firm—McAndrews, Held & Malloy, Ltd.

(57) ABSTRACT

An acoustic wave sensor/resonator utilizes a torsional wave trapped in an acoustic wave cavity that is formed in a noncylindrical substrate. An acoustic wave transducer is positioned adjacent the acoustic wave cavity off of the centerline of the cavity and in a plane parallel to a planar surface of the acoustic wave cavity to generate the torsional wave. The acoustic wave transducer can be a piezoelectric transducer or an electromagnetic transducer. Further, the torsional wave can be generated by a single transducer or multiple transducers.

47 Claims, 3 Drawing Sheets

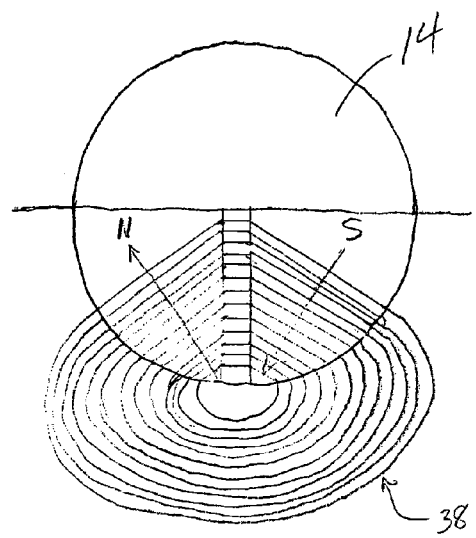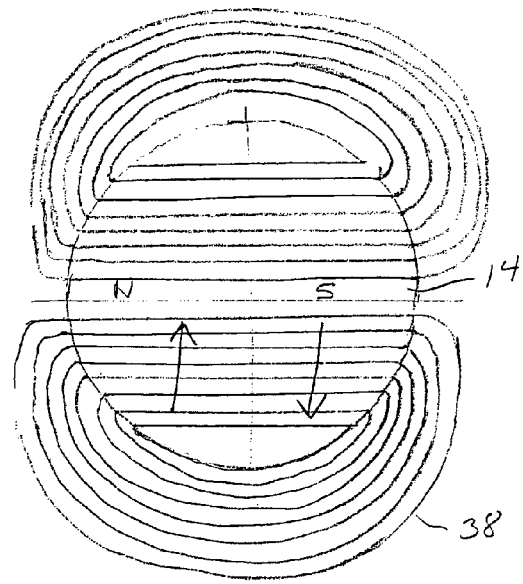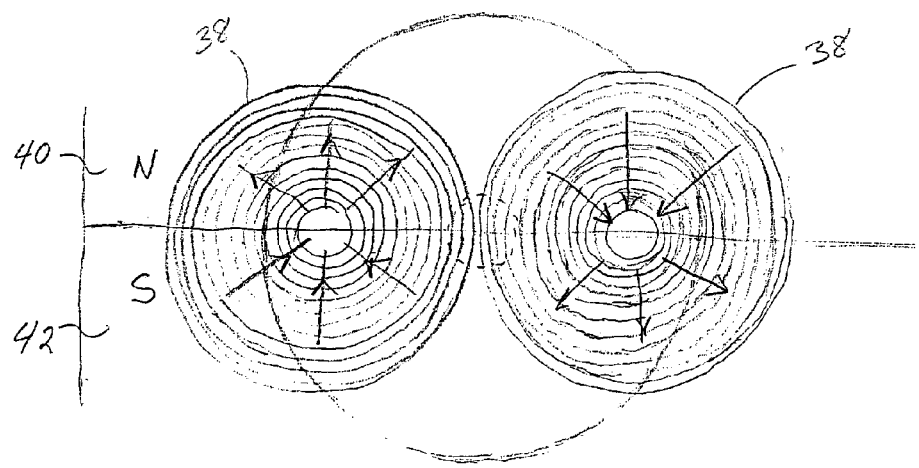

TORSIONAL ACOUSTIC WAVE SENSOR

CROSS-REFERENCE TO RELATED APPLICATIONS

This application is related to the following patent applications: U.S. patent application entitled "Acoustic Wave Touch Actuated Switch," Ser. No. 09/998,355, filed Nov. 20, 2001; U.S. patent application entitled "Acoustic Wave Sensor With EMAT Drive," Ser. No. 10/245,246, filed Sep. 17, 2002; and U.S. patent application entitled "Acoustic Wave Touch Detection Circuit and Method," Ser. No. 10/454,003 filed Jun. 4, 2003.

STATEMENT REGARDING FEDERALLY SPONSORED RESEARCH OR DEVELOPMENT

N/A

FIELD OF THE INVENTION

The present invention relates to an acoustic wave sensor that utilizes a trapped acoustic wave that is sensitive to an event such as a touch but that is insensitive to water and to variations in water level and more particularly to an acoustic wave sensor or resonator that utilizes a torsional wave trapped in an acoustic wave cavity formed in a noncylindrical substrate.

BACKGROUND OF THE INVENTION

There is a substantial need for touch actuated switches and acoustic resonators that are rugged and explosion proof, operate in the presence of liquids, have low power consumption, withstand aggressive sterilization procedures and are inexpensive. Known switches that attempt to meet these needs but fail include the following. A Qprox switch made by Quantum Research Group senses the presence of touch through a charge transfer effect. This switch is sensitive to conductive fluids and/or an ionizing atmosphere and can be made inoperable thereby. Further, the enclosure through which touch is sensed cannot be made of an electrically conducting material, so that metals and the like cannot be used. Piezoelectric switches such as supplied by Schurter or Wilson-Hurd, operate by transferring finger pressure via a metal overlay to a piezoelectric element which generates a voltage when compressed. This type of switch is expensive compared to a standard membrane switch and shares the disadvantages of membrane switches in that holes in the housing or enclosure are required to accommodate the switch. Further, the metal overlay is necessarily thin, so that the piezoelectric element is relatively unprotected against blows to the overlay. Another type of switch shown in U.S. Pat. No. 5,149,986 is based on the absorption of sound in a glass, ball-shaped button when the button is touched. In operation, a transducer sends sound waves into the glass balls and then receives back the echoes in a sonar type fashion. A circuit analyzes the echoes to determine whether the echoes have been reduced indicating a touch. This type of switch is relatively expensive and again requires openings in the housing or enclosure in which the switch is to be mounted.

An acoustic wave switch such as shown in U.S. Pat. No. 5,673,041 includes an ultrasonic piezoelectric transducer mounted on a surface of a substrate opposite a touch surface of the substrate. The transducer generates an ultrasonic wave that propagates in a direction across the thickness of the substrate to the touch surface and reflects off of the touch surface back to the transducer. The ultrasonic wave appears to be a compressional wave. A touch on the touch surface changes the acoustic reflectivity of the surface and changes the impedance of the transducer. The acoustic energy in this switch is not confined and spreads out into the plane of the substrate. As such, the ratio of the stored energy to lost or dissipated energy over a complete cycle, referred to as the Q of the switch, is inherently low and an extremely complex touch detection circuit is required to discriminate between a touch and the absence of a touch. Moreover, the use of compressional waves in this switch is undesirable due to their sensitivity to liquids and other contaminants which can render the switch inoperable.

Also known are acoustic wave touch panels that employ reflective gratings or arrays to reflect portions of an acoustic wave across a touch surface along parallel paths of differing lengths. These devices use a transparent substrate that can overlay a display to provide a touch screen or the like. Examples of such touch sensors are shown in U.S. Pat. Nos. 4,645,870 and 4,700,176 which utilize surface acoustic waves. These systems are undesirable, however, because surface acoustic waves are sensitive to liquids, sealing compounds and other contaminants that can render the panel inoperable and difficult to seal effectively. Another acoustic wave touch panel using reflective arrays is shown in U.S. Pat. No. 5,177,327. This touch panel uses shear waves and in particular the zeroth order horizontally polarized shear wave. Although this touch position sensor is insensitive to liquids and contaminants, touch position sensors that use reflective gratings or arrays and the associated touch detection circuitry are, in general, too expensive to use for an individual switch or for a small number of switches on a panel. Moreover, because the shear wave transducer in this latter system is mounted on a side of the panel to generate a shear wave that propagates in the plane of the substrate, an opening in the enclosure or housing is required to accommodate the panel. U.S. Pat. No. 5,573,077 also uses zeroth order horizontally polarized shear waves, but instead of reflective gratings, discrete transducers are used to propagate the shear waves along parallel paths extending across the substrate.

An acoustic wave switch that overcomes the above problems utilizes an acoustic wave cavity and an acoustic wave transducer to generate a resonant acoustic wave that is substantially trapped in the cavity as disclosed in U.S. patent application Ser. No. 09/998,355 filed Nov. 20, 2001. As discussed therein, the acoustic wave switch utilizes a shear wave having a harmonic mode of one or greater. Although it was believed that this acoustic wave switch was insensitive to water, it has been found that the switch is sensitive to water at a level that is a multiple of ½ $\lambda$, where $\lambda$ is the wavelength of the acoustic wave in water. It is believed that this sensitivity to water is due to flexural modes, that is a mode with vertical displacement component, generated in the acoustic wave cavity with the trapped shear wave. More specifically, because the shear wave is trapped, particles are moving faster in the interior of the acoustic wave cavity than at the edge of the cavity. This results in a "bulge" of particles that creates a vertical component in the trapped acoustic wave in addition to the transverse shear component. It is this vertical component that causes flexural motion and makes the acoustic wave switch sensitive to water. As a result of this sensitivity, when the shear acoustic wave switch is used in the presence of water, the level of which varies, such as when the switch is used outdoors in rain, the water can cause the switch to have a response that flickers. Although this flicker problem can be overcome by software processing as disclosed in the co-pending patent application entitled "Acoustic Wave Touch Detection Circuit and Method," Ser. No. 10/454,003, filed Jun. 4, 2003, it is desirable to have a switch or acoustic wave sensor that is insensitive to water at any level and that is insensitive to variations in water level.

It is noted that, besides the trapping of shear waves in a plate, it has been known that torsional waves could be trapped in a solid cylinder as described in the article "Trapped Torsional Modes In Solid Cylinders" by Ward Johnson, B. A. Auld and E. Segal, J. Acoust. Soc. Am. 100 (1), July 1996. One application of a torsional mode trapped in a cylinder is an acoustic resonator for measuring force as shown in U.S. Pat. No. 5,813,280 to Johnson et al. However, the cylindrical body, in which the torsional wave is trapped, greatly limits the application and use of trapped torsional modes.

BRIEF SUMMARY OF THE INVENTION

In accordance with the present invention, the disadvantages of prior switches and acoustic wave sensors and resonators as discussed above have been overcome. In accordance with the present invention, an acoustic wave sensor or resonator utilizes a trapped acoustic wave that is insensitive to variations in water level on the sensor/resonator surface.

In one embodiment of the present invention, an acoustic wave sensor includes an acoustic wave cavity formed in a noncylindrical substrate and defined by an area having a mass per surface area that is greater than the mass per surface area of the substrate adjacent to the acoustic wave cavity. At least one transducer is positioned with respect to the acoustic wave cavity in the noncylindrical substrate to generate a torsional acoustic wave in the acoustic wave cavity.

In accordance with one embodiment of the present invention, the transducer is mounted on a surface of the acoustic wave cavity off-center with respect to a centerline of the cavity and such that the length of the transducer is at an angle with respect to a radius of the acoustic wave cavity. In accordance with another embodiment of the present invention, at least one electromagnetic acoustic transducer is positioned adjacent a surface of the acoustic wave cavity wherein the transducer includes a coil that is off-center with respect to the centerline of the acoustic wave cavity and wherein the coil lies in a plane that is parallel to a planar surface of the acoustic wave cavity.

In accordance with a further embodiment of the present invention, an acoustic wave sensor includes an acoustic wave cavity formed in a noncylindrical substrate and defined by a raised area with a generally circular peripheral edge. At least one transducer generates an acoustic wave substantially trapped in the acoustic wave cavity wherein the transducer is positioned off-center with respect to the centerline of the acoustic wave cavity.

In accordance with still another embodiment of the present invention, an acoustic wave resonator includes an acoustic wave cavity formed in a substrate and defined by an area having an increased mass, the acoustic wave cavity having a first surface and a second surface opposite the first surface, wherein at least one of the first and second surfaces is generally planar. At least one transducer is positioned adjacent the first or the second surface of the acoustic wave cavity to generate a resonant torsional acoustic wave in the acoustic wave cavity.

These and other advantages and novel features of the present invention, as well as details of an illustrated embodiment thereof, will be more fully understood from the following description and drawings.

BRIEF DESCRIPTION OF THE SEVERAL VIEWS OF THE DRAWING

FIG. 5 is a bottom view of another embodiment of an acoustic wave sensor/resonator with an alternative coil configuration for an electromagnetic transducer generating a torsional wave trapped in an acoustic wave cavity formed in a noncylindrical substrate;

FIG. 6 is a bottom view of a further embodiment of an acoustic wave sensor/resonator with two electromagnetic acoustic transducers for generating a torsional wave trapped in an acoustic wave cavity formed in a noncylindrical substrate; and FIG. 7 is a bottom view of still another embodiment of an acoustic wave sensor/resonator with two electromagnetic acoustic transducers utilized to generate a torsional wave in an acoustic wave cavity in a noncylindrical substrate.

DETAILED DESCRIPTION OF THE INVENTION

Figure 1:
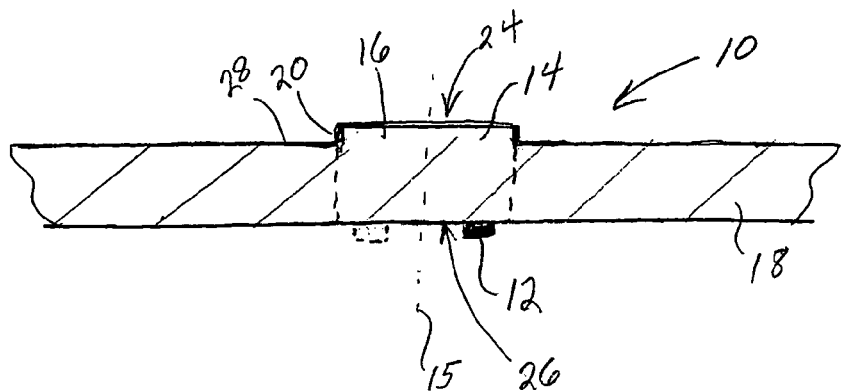
FIG. 1 is a side, cross-sectional view of an acoustic wave sensor/resonator of the present invention with one or two piezoelectric transducers mounted on an acoustic wave cavity formed in a noncylindrical substrate, the transducers being positioned off of the centerline of the cavity so as to generate a torsional acoustic wave trapped in the acoustic wave cavity.

An acoustic wave sensor or resonator 10, 11, in accordance with the present invention as shown in FIGS. 1–4, includes a transducer 12, 13 positioned adjacent an acoustic wave cavity 14 such that the transducer 12, 13 is off-center with respect to the centerline 15 of the cavity 14 so as to generate a trapped or resonant torsional acoustic wave in the acoustic wave cavity 14. The acoustic wave cavity 14 is formed in a noncylindrical substrate 18 wherein the transducer 12, 13 generating the trapped torsional acoustic wave is in a plane that is parallel to a planar surface 26 of the acoustic wave cavity 14. It has been found that a trapped, torsional acoustic wave generated in accordance with the present invention is insensitive to water. That is, an acoustic wave touch sensor, for example, utilizing a trapped torsional wave generated in accordance with the present invention will not erroneously register a sensed event when only water is present where the water is at a level that is a multiple of ½ λ, the wavelength of the wave, or where the water level is varying.

The acoustic wave cavity 14 is defined by a raised area 16, 16' the cavity extending through the thickness of a noncylindrical substrate 18 under the surface 24 of the raised area 16, 16'. The acoustic wave cavity 14 is formed on the substrate 18 by an area of increased mass such that the mass per unit surface area of the cavity 14 is greater than the mass per unit surface area of the substrate immediately adjacent the cavity 14. It is noted, that the acoustic wave cavity can also be defined by an area of increased mass that is not raised above the substrate. Such cavities can be formed, for example, by depositing a thin layer of material on the surface of the substrate in an area defining the acoustic wave cavity. Such cavities can also be formed with materials of greater mass than the substrate throughout the cavity or in a portion thereof.

Figure 3:
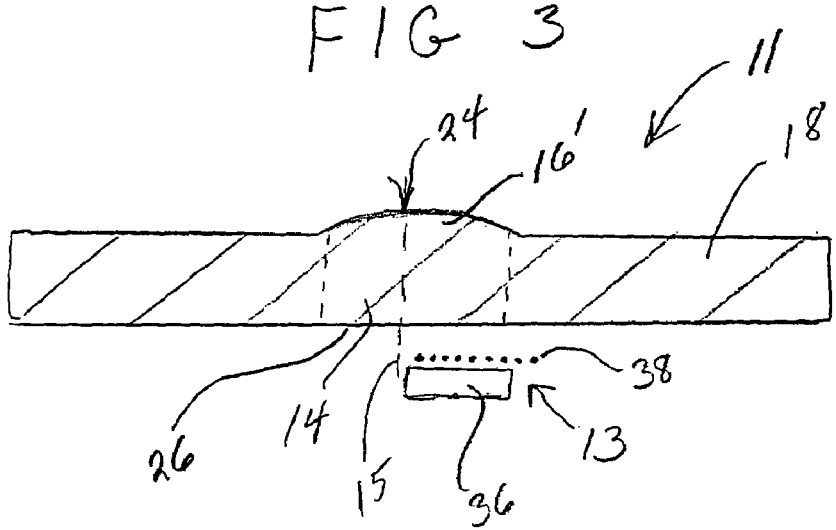
FIG. 3 is a cross-sectional view of an acoustic wave sensor/resonator in accordance with another embodiment of the present invention utilizing an electromagnetic acoustic transducer positioned adjacent an acoustic wave cavity formed in a noncylindrical substrate but off the centerline of the acoustic wave cavity so as to generate a torsional acoustic wave trapped in the cavity.

The raised area defining the acoustic wave cavity may be square, rectangular or other shapes. However, in a preferred embodiment, the raised area has a circular circumference or peripheral edge 20. The raised area 16 may have a flat surface 24 as shown in FIG. 1 or it may have a curved surface such as a dome. In FIG. 3, the acoustic wave cavity 14 is defined by a raised area 16' having the shape of a truncated dome. Although the raised areas 16 and 16' shown in FIGS. 1 and 3 are depicted as an integral part of the noncylindrical substrate 18, the raised area may also be formed as a separate piece such as a decal that is bonded to the substrate. In such an embodiment, the raised area may be formed of the same material as the substrate or of a different material. Moreover, although the transducers 12 and 13 are shown adjacent a surface 26 of the acoustic wave cavity opposite the surface 24 of the raised area of the cavity 14, the transducer 12, 13 can be mounted adjacent the raised area as well.

The height and geometry of the acoustic wave cavity 14 that will support a trapped or resonant torsional acoustic wave is the same as the height and geometry requirements of an acoustic wave cavity supporting a trapped shear wave as described in U.S. patent application Ser. No. 09/998,355, filed Nov. 20, 2001 and incorporated herein by reference. As described therein, for a shear wave having a harmonic mode, n greater than or equal to 1, the thickness of the cavity from the surface 24 to the surface 26, $b_c$, should be greater than ½ λ, where λ is the wavelength of the fundamental, zeroth order mode. For shear waves having a harmonic mode of $n \geq 1$, separate cutoff frequencies exist for the acoustic cavity and the adjacent region of the substrate. These cutoff frequencies, designated $f_c$ and $f_s$ respectively, determine the frequency range in which standing waves, and hence resonance, is possible. For wave frequencies below $f_c$, no waves propagate. For wave frequencies between $f_c$ and $f_s$, standing waves can form because of reflections at the acoustic cavity boundaries. At wave frequencies above $f_s$, the waves will not be substantially trapped within the acoustic cavity and will propagate throughout the substrate. Thus, at frequencies above $f_s$, resonance in the acoustic cavity is suppressed due to substantial leakage of acoustic energy into the surrounding areas in the substrate. The cut-off frequencies $f_c$ and $f_s$ are given by the following formulas.

$$f_c = \frac{nV_s}{2b_c} \quad f_s = \frac{nV_c}{2b_s}$$

where $b_c$ is the thickness of the acoustic cavity; $b_s$ is the substrate thickness in the area adjacent the acoustic cavity; $V_s$ is the velocity of the zeroth order mode shear wave in the substrate; $V_c$ is the velocity of the zeroth order mode shear wave in the cavity and n is the order of the harmonic mode of the generated shear.

In a preferred embodiment, the cavity is operated in only a single mode. To accomplish this in practice, the geometry of the acoustic cavity is such that the ratio of the length to thickness of the cavity satisfies the following equation where the length is designated as 2a.

$$\frac{2a}{b_c} \leq \frac{1}{n}\sqrt{\frac{2b_s}{h_c}}$$

where $h_c$ is the height of the raised area defining the cavity such that $h_c = b_c - b_s$. Similarly, the width w, of the acoustic cavity should satisfy the same relationship as follows.

$$\frac{w}{b_c} \leq \frac{1}{n}\sqrt{\frac{2b_s}{h_c}}$$

In order to generate a shear wave in such an acoustic wave cavity, a piezoelectric transducer is centered on the cavity centerline. To generate a shear wave in an acoustic wave cavity having a circular peripheral edge, the transducer is centered on the cavity such that the length of the transducer lies along a diameter of the acoustic wave cavity. In accordance with the present invention, as shown in FIGS. 1–7, it has been found that for an acoustic wave cavity formed as described above, by positioning the acoustic wave transducer such that the center of the transducer is off-center with respect to the centerline of the acoustic wave cavity as described in detail below, a torsional acoustic wave can be generated in the acoustic wave cavity 14.

Figure 2:
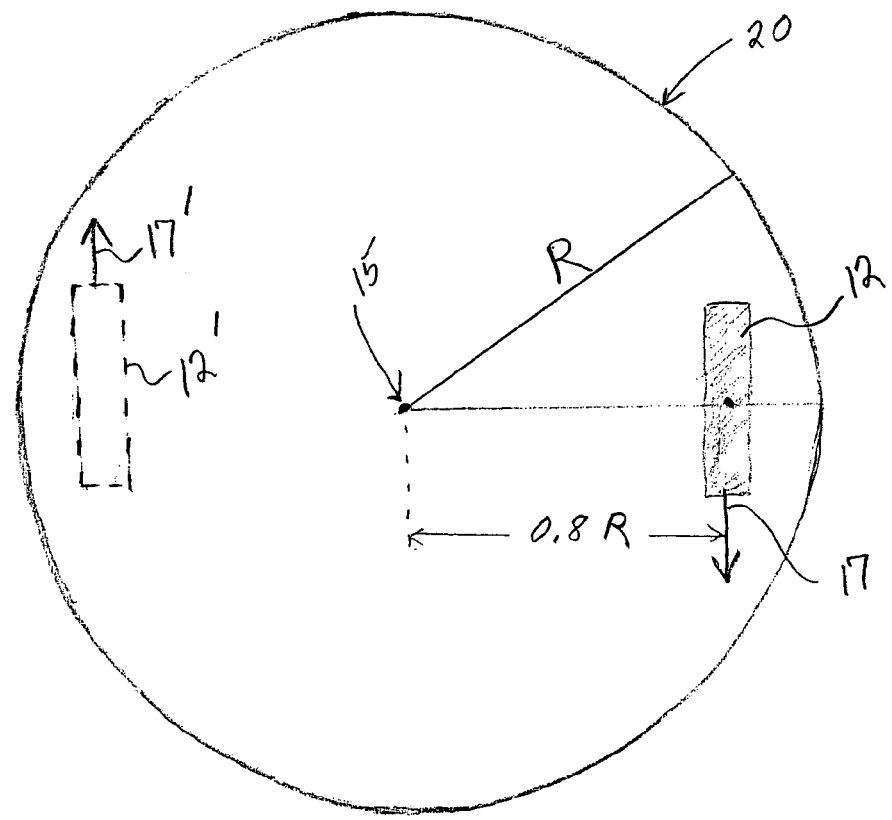
FIG. 2 is a bottom view of the acoustic wave cavity of the sensor/resonator shown in FIG. 1 and illustrating the placement of one or two piezoelectric transducers to generate a torsional acoustic wave in a noncylindrical substrate.

For an acoustic wave cavity defined by a raised area having a peripheral edge that is perpendicular to the adjacent surface 28 of the substrate 18 as shown in FIG. 1, the preferred placement of the transducer 12 for generating a trapped torsional wave is at a distance from the cavity centerline 15 of 0.8 times the radius R of the acoustic wave cavity 14. More particularly, as shown in FIG. 2, the transducer 12, which in this embodiment is a piezoelectric transducer, is mounted on the acoustic wave cavity 14 such that the center of the transducer is located on a radius of the cavity at a distance from the centerline 15 that is 0.8 times the radius R of the acoustic wave cavity 14 with the length of the transducer 12 extending at a right angle with respect to the radius of the acoustic wave cavity 14. It is noted that, for an acoustic wave cavity having a peripheral edge that is not perpendicular to the adjacent surface 28, such as the peripheral edge of a dome shaped raised area, the placement of the center of the transducer 12 is preferably at a distance from the centerline 15 of 0.6 times the radius R of the acoustic wave cavity. It should be appreciated that the distance of the center of the transducer 12 from the centerline can be outside of the range 0.6 R to 0.8 R and still generate a torsional acoustic wave. The range of 0.6 R to 0.8 R has been found to be the preferred distance from the cavity centerline for an acoustic wave cavity described above.

Although the presence of a torsional acoustic wave trapped in an acoustic wave cavity and the presence of a transverse shear acoustic wave trapped in an acoustic wave cavity can be determined by a number of different methods, one method is as follows. First, it should be appreciated that trapped acoustic wave modes are standing waves and standing waves have nodes and antinodes. One way to detect the position of a node on an acoustic wave cavity is to slide a pointed acoustic wave absorbing stylus, such as a toothpick, across the acoustic wave cavity surface 24 and to look at the impedance peak of the signal representing the acoustic wave energy trapped in the cavity where the signal is provided by the transducer 12, 13. When the stylus is over a node, that is, over a place of maximum amplitude, maximum absorption of the acoustic wave by the stylus is obtained and the impedance peak dips. By moving the stylus across the surface 24 of the acoustic wave cavity and marking the spots where maximum acoustic wave absorption occurs, an image or map of nodal lines can be obtained. For a torsional wave trapped in the acoustic wave cavity, the nodal lines are circles. The circular nodal lines are typically centered on the acoustic wave cavity 14. This is opposed to the nodal lines that are obtained when a shear wave is generated as by a center bonded piezoelectric transducer. For such a shear wave, the nodal lines are linear and extend parallel to the length of the transducer.

Although a torsional wave can be generated in the acoustic wave cavity 14 formed in a noncylindrical substrate 18 by a single transducer positioned with respect to the acoustic wave cavity as described above, multiple transducers may be used to generate a torsional wave as well. The dashed line 12' in FIGS. 1 and 2 represents the positioning of a second transducer in a two transducer embodiment for generating a trapped torsional wave. In this embodiment, the centers of the transducers 12, 12' are positioned on a diameter of the acoustic wave cavity on opposites sides of the centerline 15 and at a distance therefrom of 0.8 times the radius R of the acoustic wave cavity in this example. Again, the length of each of the transducers 12, 12' is at an angle with respect to the diameter of the acoustic wave cavity, the angle preferably being 90°. The polarity of the transducer 12' as shown by the arrows 17' is preferably opposite the polarity of the transducer 12 depicted by the arrow 17 so that when both transducers are driven, a torsional acoustic wave is generated in the acoustic wave cavity 14. Additional piezoelectric transducers can be added anywhere about the acoustic wave cavity surface 26 at a distance from the centerline of 0.8 times the radius R of the acoustic wave cavity in this example. For correct polarity alignment to generate a torsional acoustic wave, the arrows representing the polarity of the piezoelectric transducers, should all be pointing in a clockwise direction. Alternatively, the arrows representing the polarities of the transducers can all point in a counter-clockwise direction in order to generate a torsional mode in the acoustic wave cavity 14.

Figure 4:
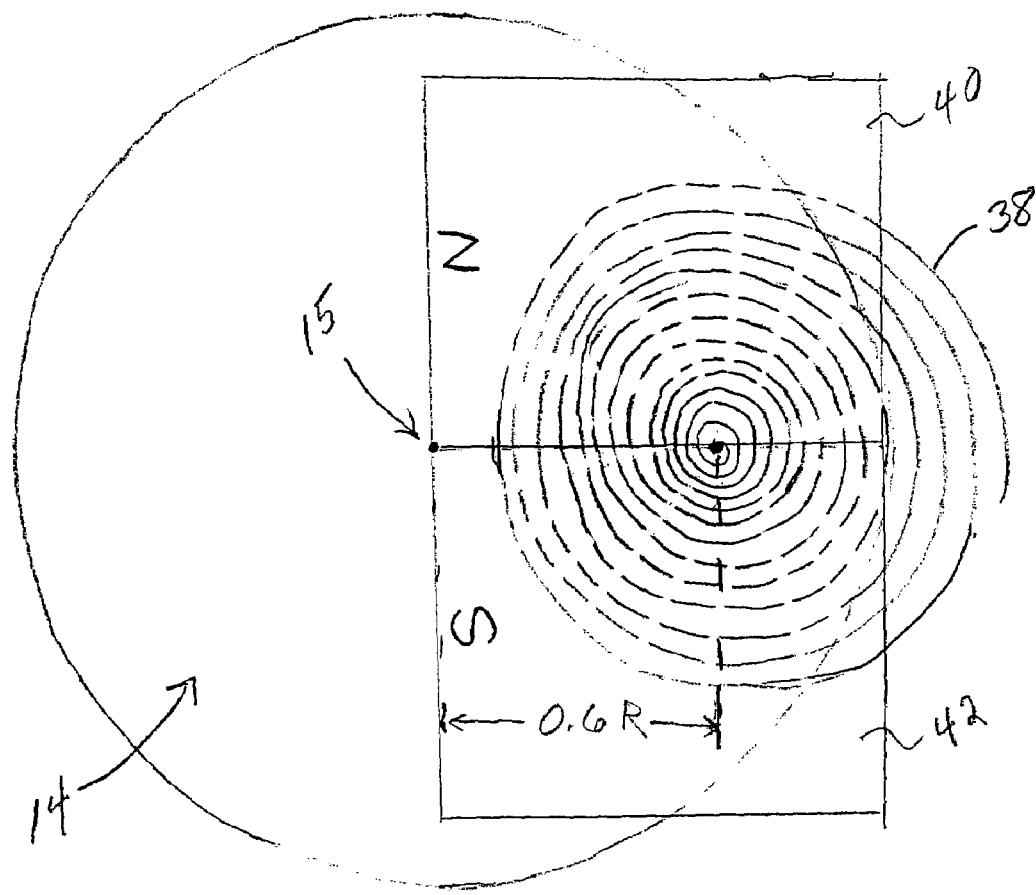
FIG. 4 is a bottom view of the acoustic wave sensor shown in FIG. 3 illustrating the positioning of the transducer coil and a pair of magnets.

As shown in FIGS. 3 and 4, the transducer 13 is an electro-magnetic acoustic transducer 32 that includes one or more magnets 36 and a coil 38 where the coil 38 is in a plane which is parallel to the planar surface 26 of the acoustic wave cavity 14 and substrate 18. As noted above, the transducer 32 may be positioned adjacent either the planar surface 26 or the non-planar surface 24 of the raised area 16'. The transducer 13 is positioned off-center with respect to the centerline 15 of the acoustic wave cavity 14 such that the center of the coil 38 is a distance from the centerline of the cavity 14 in order to generate a trapped or resonant torsional acoustic wave in the acoustic wave cavity 14 formed in the noncylindrical substrate 18. As shown in FIG. 3, because the raised area 30 has a peripheral edge that is not perpendicular to the adjacent surface of the substrate 18, the center of the coil 38 is at a preferred distance from the centerline 15 of 0.6 times the radius R of the acoustic wave cavity 14. It should be appreciated that, if the raised area defining the acoustic wave cavity has a peripheral edge that is perpendicular to the adjacent surface of the substrate 18, then the center of the coil 38 is preferably at a distance from the centerline 15 of 0.8 times the radius R of the acoustic wave cavity. As used herein, the center of an electromagnetic acoustic wave transducer is the center of the coil. FIG. 4 also illustrates the positioning of a pair of magnets 40 and 42 underneath the coil 38 and the acoustic wave cavity 14. The magnets 40 and 42 are positioned with the North pole of the magnet 40 adjacent to the South pole of the magnet 42.

Various coil and magnet configurations can be used to generate a torsional acoustic wave in an acoustic wave cavity 14 that is formed in a noncylindrical substrate 18 as shown in FIGS. 5–7. In each of these embodiments, a portion of the electromagnetic transducer coil is adjacent the acoustic wave cavity 14 but the center of the coil is off-center with respect to the centerline of the acoustic wave cavity. Moreover, as shown in FIGS. 6 and 7, multiple electromagnetic transducers can be used to generate a torsional acoustic wave as well as a single electromagnetic acoustic wave transducer as depicted in FIGS. 3 and 4. As used herein, a single electromagnetic acoustic transducer will have a single coil, whereas multiple electromagnetic acoustic wave transducers have multiple coils but may share one or more magnets. That is, the number of transducers is generally equal to the number of coils. Further, the center of each transducer is the center of the respective coil. Where multiple transducers are used, such as shown in FIG. 7, the current should flow in opposite directions in each of the coils so as to produce the Lorentz forces that are depicted by the arrows in FIG. 7. The arrows in FIGS. 5 and 6 depict the Lorentz forces in those embodiments as well.

The acoustic wave sensor/resonator of the present invention can sense an event such as a touch on a surface 24 of the sensor without any interference caused by water. A suitable touch detection circuit for analyzing the trapped torsional wave to detect a touch is described in the co-pending United States patent application entitled "Acoustic Wave Touch Detection Circuit and Method," Ser. No. 10/454,003, filed Jun. 4, 2003 and incorporated herein by reference. The acoustic wave sensor/resonator can also be used to sense other events as well such as the presence of a particular component in a liquid for a liquid phase sensor wherein the sensor is insensitive to variations in the level of the liquid on the sensor. These are just a few of the applications for which the acoustic wave sensor/resonator of the present invention can be used.

Many modifications and variations of the present invention are possible in light of the above teachings. For example, as discussed above, the transducers can be off-center from the acoustic wave cavity by more or less than 0.6 to 0.8 times the cavity radius and still generate a torsional acoustic wave. Further, as noted above, the acoustic wave cavity can have a peripheral edge that is not circular. In such an embodiment, the transducer should be positioned off-center from the acoustic wave cavity and such that the length of the transducer such as a piezoelectric transducer is not parallel to a peripheral edge of the cavity. Thus, it is to be understood that, within the scope of the appended claims, the invention may be practiced otherwise than as described hereinabove.

The invention claimed is:

1. An acoustic wave sensor comprising:
an acoustic wave cavity formed in a noncylindrical substrate and defined by an area having a mass per surface area that is greater than the mass per surface area of the substrate adjacent to the acoustic wave cavity; and at least one transducer positioned with respect to the acoustic wave cavity to generate a torsional acoustic wave in the acoustic wave cavity.

2. An acoustic wave sensor as recited in claim 1 wherein the area of greater mass defining the acoustic wave cavity includes a raised area on the substrate.

3. An acoustic wave sensor as recited in claim 2 wherein the raised area has a circular periphery.

4. An acoustic wave sensor as recited in claim 2 wherein the raised area is a dome.

5. An acoustic wave sensor as recited in claim 4 wherein the dome is a truncated dome.

6. An acoustic wave sensor as recited in claim 2 wherein the raised area is integral with the substrate.

7. An acoustic wave sensor as recited in claim 2 wherein the raised area is bonded to the substrate.

8. An acoustic wave sensor as recited in claim 1 wherein the noncylindrical substrate is planar in the area of the acoustic wave cavity and the area immediately adjacent thereto.

9. An acoustic wave sensor as recited in claim 1 wherein the noncylindrical substrate is generally planar.

10. An acoustic wave sensor as recited in claim 1 wherein the sensor includes a piezoelectric transducer mounted on a surface of the acoustic wave cavity.

11. An acoustic wave sensor as recited in claim 1 wherein the sensor includes a plurality of piezoelectric transducers.

12. An acoustic wave sensor as recited in claim 11 wherein transducers mounted on opposite sides of the substrate have opposite polarities.

13. An acoustic wave sensor as recited in claim 1 wherein the sensor includes an electro-magnetic acoustic transducer adjacent a surface of the acoustic wave.

14. An acoustic wave sensor as recited in claim 1 wherein the sensor includes a plurality of electro-magnetic acoustic transducers.

15. An acoustic wave sensor as recited in claim 1 wherein the transducer is positioned off-center with respect to a centerline of the acoustic wave cavity and spaced inwardly from a peripheral edge of the cavity.

16. An acoustic wave sensor as recited in claim 1 wherein the transducer is positioned at a distance from a centerline of the acoustic wave cavity of approximately 0.6 to 0.8 times the distance from the center of the cavity to a peripheral edge of the cavity.

17. An acoustic wave sensor comprising:
an acoustic wave cavity formed in a noncylindrical substrate and defined by an area with a generally circular peripheral edge and having a mass per surface area that is greater than the mass per surface area of the substrate adjacent to the acoustic wave cavity; and
at least one transducer generating an acoustic wave substantially trapped in the acoustic wave cavity, the transducer being positioned off-center with respect to a centerline of the acoustic wave cavity.

18. An acoustic wave sensor as recited in claim 17 wherein the transducer is positioned at a distance from the center of the acoustic wave cavity of approximately 0.6 to 0.8 times the distance from the centerline of the cavity to a peripheral edge of the cavity.

19. An acoustic wave sensor as recited in claim 17 wherein the noncylindrical substrate is planar in the area of the acoustic wave cavity and the area immediately adjacent thereto.

20. An acoustic wave sensor as recited in claim 17 wherein the noncylindrical substrate is generally planar.

21. An acoustic wave sensor as recited in claim 17 wherein the sensor includes a piezoelectric transducer mounted on a surface of the acoustic wave cavity.

22. An acoustic wave sensor as recited in claim 17 wherein the sensor includes a plurality of piezoelectric transducers.

23. An acoustic wave sensor as recited in claim 22 wherein transducers mounted on opposite sides of the substrate have opposite polarities.

24. An acoustic wave sensor as recited in claim 17 wherein the sensor includes an electro-magnetic acoustic transducer adjacent a surface of the acoustic wave.

25. An acoustic wave sensor as recited in claim 17 wherein the sensor includes a plurality of electro-magnetic acoustic transducers.

26. An acoustic wave sensor comprising:
an acoustic wave cavity formed in a noncylindrical substrate and defined by a raised area with a generally circular peripheral edge; and
at least one transducer generating an acoustic wave substantially trapped in the acoustic wave cavity, the transducer being positioned off-center with respect to a centerline of the acoustic wave cavity.

27. An acoustic wave sensor as recited in claim 26 wherein the transducer is positioned at a distance from the centerline of the acoustic wave cavity of approximately 0.6 to 0.8 times the distance from the centerline of the cavity to a peripheral edge of the cavity.

28. An acoustic wave sensor as recited in claim 26 wherein the raised area is a dome.

29. An acoustic wave sensor as recited in claim 28 wherein the dome is a truncated dome.

30. An acoustic wave sensor as recited in claim 26 wherein the raised area is integral with the substrate.

31. An acoustic wave sensor as recited in claim 26 wherein the raised area is bonded to the substrate.

32. An acoustic wave sensor as recited in claim 26 wherein the sensor includes a piezoelectric transducer mounted on a surface of the acoustic wave cavity.

33. An acoustic wave sensor as recited in claim 26 wherein the sensor includes a plurality of piezoelectric transducers.

34. An acoustic wave sensor comprising:
an acoustic wave cavity formed in a noncylindrical substrate and defined by a raised area with a generally circular peripheral edge; and
at least one transducer generating an torsional acoustic wave substantially trapped in the acoustic wave cavity, the transducer being positioned off-center with respect to a centerline of the acoustic wave cavity.

35. An acoustic wave sensor as recited in claim 34 wherein the transducer is positioned at a distance from the centerline of the acoustic wave cavity of approximately 0.6 to 0.8 times the distance from the centerline of the cavity to a peripheral edge of the cavity.

36. An acoustic wave sensor comprising:
an acoustic wave cavity formed in a noncylindrical substrate and defined by an area with a generally circular peripheral edge and having a mass per surface area that is greater than the mass per surface area of the substrate adjacent to the acoustic wave cavity; and
at least one transducer generating an torsional acoustic wave substantially trapped in the acoustic wave cavity, the transducer being positioned off-center with respect to a centerline acoustic wave cavity.

37. An acoustic wave sensor as recited in claim 36 wherein the transducer is positioned at a distance from the centerline of the acoustic wave cavity of approximately 0.6 to 0.8 times the distance from the centerline of the cavity to a peripheral edge of the cavity.

38. An acoustic wave sensor comprising:
   an acoustic wave cavity formed in a noncylindrical substrate and defined by an area having a mass per surface area that is greater than the mass per surface area of the substrate adjacent to the acoustic wave cavity; and
   at least one transducer generating an acoustic wave that is substantially trapped in the acoustic wave cavity and that is insensitive to water of varying levels on the acoustic wave cavity.

39. An acoustic wave sensor as recited in claim 38 wherein the acoustic wave is a torsional wave.

40. An acoustic wave sensor as recited in claim 38 wherein the transducer is positioned off-center with respect to a centerline of the acoustic wave cavity and spaced inwardly from a peripheral edge of the cavity.

41. An acoustic wave sensor as recited in claim 38 wherein the transducer is positioned at a distance from the centerline of the acoustic wave cavity of approximately 0.6 to 0.8 times the distance from the centerline of the cavity to a peripheral edge of the cavity.

42. An acoustic wave sensor as recited in claim 38 wherein the trapped acoustic wave is sensitive to a finger touch on a surface of the acoustic wave cavity.

43. An acoustic wave sensor comprising:
   an acoustic wave cavity formed in a noncylindrical substrate and defined by an area having an increased mass, the acoustic wave cavity having a first surface and a second surface opposite the first surface, at least one of said first and second surfaces being generally planar; and
   at least one transducer positioned adjacent the first or the second surface of the acoustic wave cavity to generate a torsional acoustic wave in the acoustic wave cavity.

44. An acoustic wave sensor as recited in claim 43 wherein the area of increased mass is a raised area.

45. An acoustic wave sensor as recited in claim 43 wherein the transducer is mounted on the first or second surface of the acoustic wave cavity.

46. An acoustic wave sensor as recited in claim 43 wherein the transducer is an electro-magnetic acoustic transducer.

47. An acoustic wave resonator comprising:
   an acoustic wave cavity formed in a noncylindrical substrate and defined by an area having a mass per surface area that is greater than the mass per surface area of the substrate adjacent to the acoustic wave cavity; and
   at least one transducer positioned with respect to the acoustic wave cavity to generate a resonant torsional acoustic wave in the acoustic wave cavity.

* * * * *